United States Patent
García Aparicio et al.

(10) Patent No.: US 9,283,620 B2
(45) Date of Patent: Mar. 15, 2016

(54) PARTS WITH DIFFERENT SURFACE FINISHES AND THE PROCEDURE TO OBTAIN THEM

(75) Inventors: Juan Carlos García Aparicio, Sentmenat (ES); Francesc Al Sina Font, Sentmenat (ES)

(73) Assignee: Phibo Cad-Cam, S.L., Barcelona (ES)

( * ) Notice: Subject to any disclaimer, the term of this patent is extended or adjusted under 35 U.S.C. 154(b) by 571 days.

(21) Appl. No.: 13/502,263

(22) PCT Filed: Sep. 3, 2010

(86) PCT No.: PCT/ES2010/000367
§ 371 (c)(1),
(2), (4) Date: Apr. 16, 2012

(87) PCT Pub. No.: WO2011/045451
PCT Pub. Date: Apr. 21, 2011

(65) Prior Publication Data
US 2012/0202008 A1    Aug. 9, 2012

(30) Foreign Application Priority Data

Oct. 16, 2009   (ES) .................................. 200902005

(51) Int. Cl.
| | |
|---|---|
| *B22F 3/24* | (2006.01) |
| *A61C 13/00* | (2006.01) |
| *B22F 3/12* | (2006.01) |
| *A61C 8/00* | (2006.01) |

(52) U.S. Cl.
CPC .............. *B22F 3/24* (2013.01); *A61C 13/0003* (2013.01); *A61C 13/0004* (2013.01); *B22F 3/12* (2013.01); *A61C 8/0048* (2013.01); *B22F 2003/247* (2013.01); *Y10T 428/24372* (2015.01)

(58) Field of Classification Search
None
See application file for complete search history.

(56) References Cited

U.S. PATENT DOCUMENTS

| | | | | |
|---|---|---|---|---|
| 3,718,461 | A | * | 2/1973 | Dewey .......................... 420/437 |
| 5,462,575 | A | * | 10/1995 | Del Corso ....................... 75/243 |
| 2003/0152884 | A1 | * | 8/2003 | Wiechmann et al. ............. 433/9 |
| 2008/0201008 | A1 | * | 8/2008 | Twelves et al. ............... 700/160 |
| 2008/0230397 | A1 | * | 9/2008 | Fecher et al. ................. 205/674 |
| 2008/0241798 | A1 | | 10/2008 | Holzner et al. |

FOREIGN PATENT DOCUMENTS

WO    WO 2007/084768  A1    7/2007

OTHER PUBLICATIONS

International Search Report dated Feb. 17, 2011 issued in corresponding international patent application No. PCT/ES2010/000367.
International Preliminary Report on Patentability dated Feb. 1, 2012 issued in corresponding international patent application No. PCT/ES2010/000367.

* cited by examiner

*Primary Examiner* — Jessee R. Roe
*Assistant Examiner* — Ngoclan T Mai
(74) *Attorney, Agent, or Firm* — Ostrolenk Faber LLP

(57) ABSTRACT

Disclosed are pieces that are produced by sintering, which have well-differentiated surface finish areas including rough areas resulting from the sintering process, the roughness being determined by the size of grain used in sintering, and polished areas that have undergone a three-dimensional machining process. Also, dislosed is a method that, after obtaining a file containing a representation of the piece to be produced, comprises: selecting the parts to be raised; producing the piece by means of sintering; and subsequently subjecting the piece to automatic, semi-automatic or directed programming generation so that, by means of machining, the raised parts are reduced. Consequently, the resulting piece is economical in terms of costs and exhibits a very high degree of precision in the machined areas, a tolerance 9, and improved finish, texture and finishing in the sensitive areas of the piece.

6 Claims, 4 Drawing Sheets

7

PARTS WITH DIFFERENT SURFACE FINISHES AND THE PROCEDURE TO OBTAIN THEM

CROSS REFERENCE TO RELATED APPLICATIONS

The present application is a 35 U.S.C. §371 National Phase conversion of PCT/ES2010/000367, filed Sep. 3, 2010, which claims benefit of Spanish Application No. P200902005, filed Oct. 16, 2009, the disclosures of which are incorporated herein by reference.

OBJECT OF THE INVENTION

The object of this invention is parts with a different surface finish as well as the procedure to obtain them. As the title of the invention states, the parts have different surface finishes in areas that are easily distinguished, with each area thereby providing a series of favourable features for later use.

This invention is characterised by the fact that the parts are manufactured by means of a joint procedure, in general by a sintering process at first, while afterwards certain areas of the part are machined, providing them with a different surface finish.

As regards the manufacturing procedure, this invention is characterised by the fact that the parts are manufactured by means of a sintering process and processed afterwards by means of three-dimensional machining, thereby obtaining parts manufactured by means of a sintering process with a high degree of precision and tolerance.

The procedure that is the object of the invention is also characterised by the nature and order of the stages, whereby it is possible to obtain parts by means of a sintering process with a high degree of precision and an optimal margin of tolerance.

This procedure adequately combines the advantages derived by manufacturing by means of a sintering process and manufacturing by means of three-dimensional machining, thereby obtaining parts with a very high degree of precision in certain areas, with complex geometries, thereby improving design and manufacturing times and, as a result, costs.

BACKGROUND OF THE INVENTION

The sintering process consists in thermal treatment of a powder or compacted metal, ceramic or plastic at a temperature lower than the fusion temperature of the mix, which increases the strength and the resistance of the part due to the strong bonds produced between the particles.

On the other hand, the machining process, particularly three-dimensional machining, mainly consists in cutting the machined material with a rotary tool equipped with several blades, known as teeth, lips or small plates made of hard metal. These follow forward movements in almost any direction that the workbench can move in, programmed from the workbench on which the part being machined is fastened.

In manufacturing processes of parts that require a high degree of precision and expensive materials, the sintering process has obtained an extraordinary reduction in costs and, although the tolerance and precision obtained are acceptable, these could be improved since they are conditioned by the size of the powder particles used in the sintering process. On the other hand, the amount of discarded material in machining processes such as milling is relatively large, as well as the time invested in the process, which considerably increases the cost of the manufacturing process. However, the precision obtained is quite good.

Although the manufacture of parts by means of the sintering process obtains complex parts easily, inexpensively and efficiently, the geometry of these parts may require a high degree of precision, especially in the areas that need a perfect mechanical fit with other parts. In addition, the parts manufactured so far may require that the surface of these parts have a different grade of finish in order to obtain future advantages derived from the different surface finish.

Therefore, it is the object of this invention to develop parts that can be manufactured by means of the sintering process and to obtain different degrees of precision in different areas, as well as to obtain the advantages derived from their surface finishes.

Also on the other hand, it is the object of this invention to develop a high-precision parts manufacturing method that combines the advantages of the sintering process and three-dimensional machining in which the costs are as low as possible while the precision and tolerance obtained are the best possible.

DESCRIPTION OF THE INVENTION

First, in order to achieve the goal of obtaining parts manufactured by means of a sintering process that achieves different degrees of precision in different areas, as well as the subsequent advantages derived from the surface finish, the parts that are the object of the invention are manufactured by means of a sintering process and present different surface finishes in areas that are easy to distinguish; in one area a finish obtained by the sintering process with a roughness that is the result of the grain size of the powder used in the sintering process, and in other areas a smooth finish that is the result of subjecting said part to a three-dimensional machining process, thereby obtaining a single part with two perfectly differentiated surface finishes.

As the parts present a different surface finish in areas that are easy to distinguish, three objectives are achieved:

On one hand, parts that have a high degree of precision in the areas that require a perfect mechanical fit with other parts. These areas are those that have been subjected to a three-dimensional machining process after being manufactured by means of the sintering process.

On the other hand, the degree of surface roughness is different on the various areas of the part, since some areas present a certain degree of roughness due to having been manufactured by means of a sintering process, as a result of the size of the powder particles used in their manufacture. Said roughness serves to improve fastening with other parts or materials by means of cement or similar materials.

As the part has been manufactured by means of a sintering process, parts with complex geometries can be obtained (any geometry that can be defined in space); geometries that would be impossible to obtain by means of other manufacturing techniques.

In order to obtain the proposed goal of a manufacturing process of parts at low cost and with high precision and tolerance, a manufacturing procedure has been developed that starts with a part manufactured by means of a sintering process and undergoes a series of subsequent stages that improve its precision and tolerance.

In general, all these manufacturing processes start with an STL file, although this could be applied to any other format valid for the representation of the part to be manufactured. The STL format is a standard stereolithographic format that contains a geometrical description of the object designed, using approximation by means of triangles.

Once the file is in STL format, the sensitive areas of the parts that require greater precision due to their location or function are augmented locally or in their entirety. This augmentation need not be understood literally, since it can be done with predetermined shapes or any other configuration that allows subsequent three-dimensional machining in the area of augmentation or where there is a certain shape.

Once the file has been obtained and prepared, it is then subjected to manufacture by means of the sintering process.

Afterwards, the manufactured part can be optionally subjected to an intermediate heat treatment process in order to relax the metals.

Afterwards, the original and supposedly final geometries are machined in the areas considered sensitive, whose geometry has been preserved, extracted or generated by generating programs that perform automatic, semi-automatic or directed milling (4). A very high degree of precision is obtained in the sensitive areas of the part by means of automatic machining.

This three-dimensional machining is performed in a machine that should be able to reach and reflect any point in space. The centring and referencing procedure is critical and essential at this point. The machines best equipped for this work are milling machines with five (5) controllable axes (3 for positioning and 2 for spatial direction) or those known in the market as having four plus one axes.

Finally, the part is cut and prepared for delivery.

The fact that the precision and tolerance obtained in a sintering manufacturing process is less than that obtained in a machining process is derived from the nature of the materials used and the process undertaken. Thus, when chrome and cobalt powders are used in the sintering process, the grains used are between 36 and 54 micra thick, or even higher, implying a physical compaction limit. In addition, stress, torsion and folding can be caused by the sintering process itself, which applies heat in a very short time interval of nanoseconds.

The sintered part can be rectified directly afterwards without augmentation. However, in certain situations the mill might not make contact with the material due to the difference in the wall resulting from the sintering process. Therefore, direct machining of a part obtained by means of a sintering process would not achieve the desired results.

Since the part is subjected to a local or global augmentation process, it is then possible to subject the part to a machining process that achieves exact recessing. This achieves a part with greater precision and tolerance (level 9) than a part obtained only by sintering. In addition, the quality, texture and completion of the finish are better than if it were obtained directly by the sintering process.

The parts that are object of the invention can be applied in any industry or sector that requires parts with complex geometries, that can be manufactured quickly and easily and that have a high degree of precision in certain areas. Specifically, they can be applied in the medical, dental precision machinery, automobile, aeronautic and naval sectors, for example.

The procedure that is also the object of the invention can also be applied in any industry or sector that requires parts with complex geometries, that can be manufactured quickly and easily and that have a high degree of precision in certain areas. Specifically, they can be applied in the medical, dental precision machinery, automobile, aeronautic and naval sectors, for example.

EXPLANATION OF THE ILLUSTRATIONS

To complete the description and in order to provide a fuller understanding of the characteristics of the invention, attached to this descriptive dossier is a set of drawings or illustrations. These are only presented as a guideline, taking into consideration the infinite possibilities, whether functional or aesthetic. These illustrations will provide a better understanding of the innovation and advantages of the device that is the object of the invention.

PREFERRED EMBODIMENT OF THE INVENTION

The following is a preferred embodiment of the proposed invention based on the illustrations.

Figure 1:
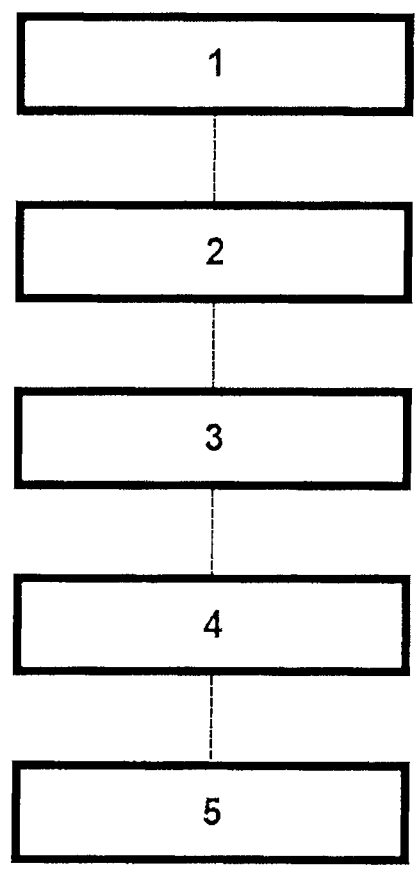
FIG. 1 shows the stages of the manufacturing process which is the object of the invention.

FIG. 1 shows the stages that make up the manufacturing process.

Figure 2:
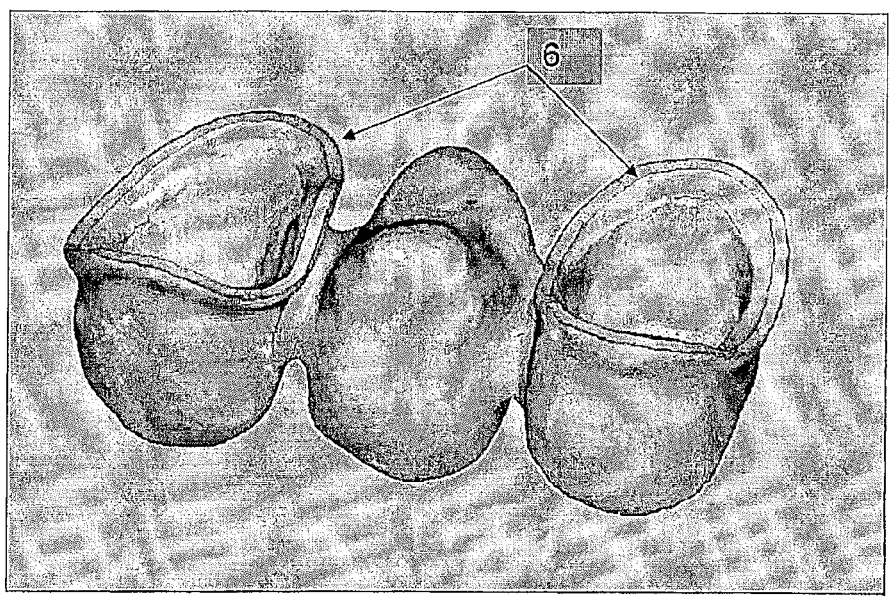
FIG. 2 shows a perspective view of a dental piece with a contour identified for augmentation.

Thus, once having received a file with a representation of the part to manufacture, partial or global augmentation (1) of certain areas is performed. This augmentation consists in defining a contour (6) of augmentation, as shown in FIG. 2, and then extending said augmentation along the selected area of the piece; in other words, as though a dental crown were being placed along the dental piece.

The purpose of this augmentation is to obtain areas of greater precision and tolerance after three-dimensional machining. In the case of dental pieces, for example, these are necessary to obtain accurate placement of elements on implants or placement of cemented dental pieces.

In one possible embodiment, the format of the file can be the STL format.

Once the file is in STL format, in which the piece is already augmented, the manufacture (2) by means of sintering is undertaken.

It is optional and not mandatory to subject the part obtained by sintering to an intermediate heat treatment process (3) in order to relax the metals after the manufacturing process. This intermediate heat treatment process consists in subjecting the part to a temperature of 1000° C. obtained by a fast ramp of temperature increase and later cooling at room temperature.

Afterwards, either after sintering (2) or after the intermediate heat treatment process (3), the part is subjected to post-processing treatment consisting in three-dimensional machining (4) using a machine with at least 5 axes, including machines known on the market as four plus one axes.

Milling (4) is performed only on the selected areas, which generally coincide with the augmented areas or on the areas with shapes for later augmentation.

Finally, the parts are cut or separated (5) from each other for subsequent delivery.

Figure 3:
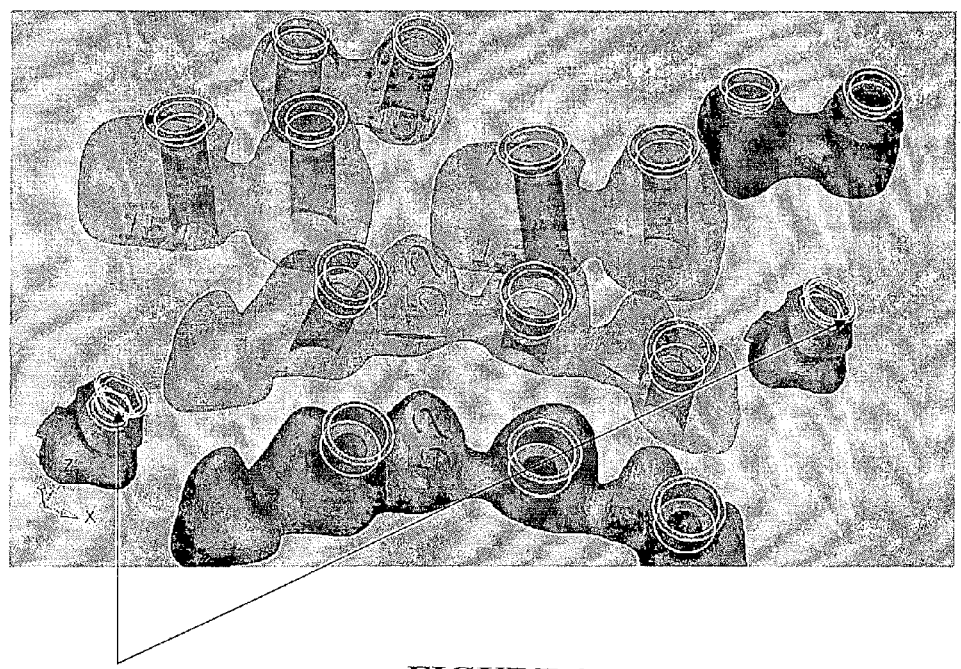
FIG. 3 shows a detailed view of the extraction of sensitive characteristics in placements on the parts after sintering.

FIG. 3 shows a set of parts, which are dental pieces in this case but could be any other kind of part. The sensitive parts have been augmented in this case to achieve accurate machined placements (7) for elements on implants or placement of cemented parts.

Figure 4:
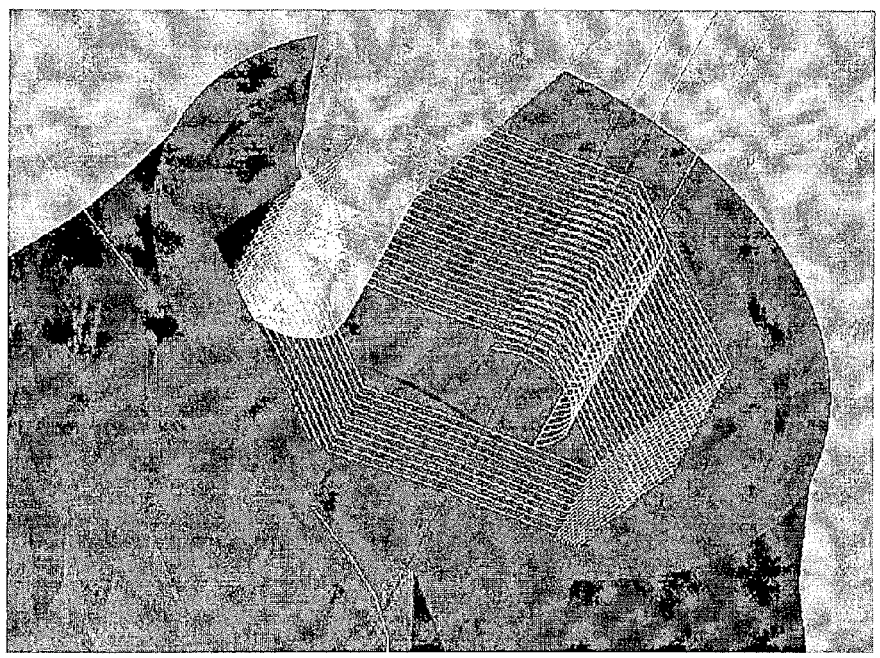
FIG. 4 shows a specific detailed view of the machining of a sensitive part of a dental piece.

FIG. 4 shows a detailed view of the machining process for accurate machined placement using milling after sintering.

The procedure described above obtains sintered parts with a high degree of precision, tolerance, quality, texture and finish, and represents a much lower cost than if the part had been obtained by milling.

The manufacturing procedure described above can be applied to all kinds of parts, such as dental pieces (crowns, bridges, skeletal parts), prostheses of all types, mechanical precision parts, in the medical, dental, precision machinery, automobile, aeronautic, naval sectors, etc.

The machinery used for sintering can be any 2, 3, 4, or 5 degree laser machine, jack laser machines, CO2 or thermal machines.

The parts obtained using the procedure described above are characterised by being manufactured by means of a sintering process and in which certain areas or all of the exterior has been treated by a milling process, resulting in greater quality, texture and finish in the sensitive areas of the part, obtaining greater precision and level 9 tolerance. Therefore, these parts present areas whose surface finish is easily distinguished, some areas with a certain roughness obtained directly by sintering and other areas are polished and smooth as a result of applying post-process three-dimensional machining.

The essence of this invention is not altered by variations in materials, shapes, sizes or layout of the composing elements, not limited to the descriptions, with this being sufficient for reproduction by an expert.

The invention claimed is:

1. A method for manufacturing a part, the method comprising:
   receiving a file for a part to be manufactured;
   partially or globally augmenting certain areas of the part selected for augmentation which are identified in the file;
   sintering the augmented part to obtain a sintered part;
   subjecting the sintered part to an intermediate heat treatment that includes heating the sintered part to a temperature of 1000° C.; and
   milling selected areas of the sintered part after the intermediate heat treatment according to a milling program,
   wherein the part is made of a chrome and cobalt alloy, and wherein the intermediate heat treatment process includes increasing the temperature to 1000° C. and subsequently cooling the heated part at room temperature.

2. The method according to claim 1, wherein the partially or globally augmenting includes defining a contour for augmentation, so as to subsequently extend said augmentation along a selected area of the part.

3. The method according to claim 1, wherein the file is a stereolithography (STL) file.

4. The method according to claim 1, wherein the milling performs milling in an automatic, semi-automatic or directed manner.

5. The method according to claim 1, wherein the part is an augmented dental piece reconstructed according to an original geometry and markings on sensitive areas, which correspond to the certain areas, and the milling is performed on the augmented dental piece either automatically or semi-automatically with a machine with at least 4 axes and an additional axis.

6. The method according to claim 1, wherein the milling program determines the milling, and requires automated reference procedures and final and augmented geometries, and wherein the milling is performed by a machine with at least 5 axes.

* * * * *